(12) United States Patent
Lee

(10) Patent No.: US 7,118,667 B2
(45) Date of Patent: Oct. 10, 2006

(54) BIOSENSORS HAVING IMPROVED SAMPLE APPLICATION AND USES THEREOF

(76) Inventor: Jin Po Lee, 7348 Melodia Ter., Carlsbad, CA (US) 92009

( * ) Notice: Subject to any disclaimer, the term of this patent is extended or adjusted under 35 U.S.C. 154(b) by 72 days.

(21) Appl. No.: 10/860,730

(22) Filed: Jun. 2, 2004

(65) Prior Publication Data

US 2005/0269214 A1    Dec. 8, 2005

(51) Int. Cl.
*G01N 27/327*    (2006.01)
(52) U.S. Cl. .............................. 205/777.5; 204/403.04; 204/403.02; 427/2.13
(58) Field of Classification Search ............ 204/ 403.4–403.15; 427/2.13; 203/777.5, 778
See application file for complete search history.

(56) References Cited

U.S. PATENT DOCUMENTS

| | | | |
|---|---|---|---|
| 4,999,582 A | 3/1991 | Parks et al. | |
| 5,120,420 A | 6/1992 | Nankai et al. | |
| 5,264,103 A | 11/1993 | Yoshioka et al. | |
| 5,288,636 A | 2/1994 | Pollmann et al. | |
| 5,320,732 A | 6/1994 | Nankai et al. | |
| 5,508,171 A | 4/1996 | Walling et al. | |
| 5,628,890 A | 5/1997 | Carter et al. | 204/403.05 |
| 5,708,247 A | 1/1998 | McAleer et al. | 204/403.05 |
| 5,759,364 A * | 6/1998 | Charlton et al. | 204/403.14 |
| 5,762,770 A | 6/1998 | Pritchard et al. | |
| 5,951,836 A | 9/1999 | McAleer et al. | 205/777.5 |
| 5,997,817 A | 12/1999 | Crismore et al. | 204/403.1 |
| 6,241,862 B1 | 6/2001 | McAleer et al. | 204/403.05 |
| 6,793,802 B1 | 9/2004 | Lee et al. | |
| 6,837,976 B1 * | 1/2005 | Cai et al. | 204/403.14 |

FOREIGN PATENT DOCUMENTS

| | | |
|---|---|---|
| EP | 0 735 363 | 10/1996 |
| EP | 0 851 224 | 7/1998 |
| EP | 0 909 952 | 4/1999 |
| JP | 02-310457 | 12/1990 |

OTHER PUBLICATIONS

Anzai et al., Anal. Chem. (1998) 70(4): 811-817.
Kureishi et al., Bioelectrochem. Bioenerg. (1999) 48(1): 95-100.
Stonehuerner et al., Biosens. Bioelectron. (1992) 7(6): 421-428.

* cited by examiner

*Primary Examiner*—Alex Noguerola
(74) *Attorney, Agent, or Firm*—Morrison & Foerster LLP

(57) ABSTRACT

The present invention relates to biosensors having improved sample application and measuring properties and their uses for detection, preferably, quantitative measurement, of analyte in a liquid sample. In particular, the invention provides for a biosensor having a sample application, reaction area and liquid soluble hydrophilic material facilitating the speed and uniformity of sample application, especially small volume sample application, via capillary flow. Methods for assaying analytes or enzymes using the biosensors are further provided.

33 Claims, 7 Drawing Sheets

BIOSENSORS HAVING IMPROVED SAMPLE APPLICATION AND USES THEREOF

FIELD OF THE INVENTION

The present invention relates to biosensors having improved sample application and measuring properties and their uses for detection, preferably, quantitative measurement, of analyte or enzyme in a liquid sample. In particular, the invention provides for a biosensor having a configuration and reagents facilitating the speed and uniformity of sample application, especially small volume sample application. Methods for assaying analytes or enzymes using the biosensors are further provided.

BACKGROUND OF THE INVENTION

A biosensor is an analytical device that comprises at least two components: an immobilized biological component responsible for the selective recognition of the test species and a suitable transducer device responsible for relaying the biological signals for further analysis. Among others, electrochemical biosensors that employ biological recognition systems and electrochemical transudation offer a possibility of quick and real-time analysis, which is particularly suited for the rapid measurement of point-of-care industry. The evolution of these devices comes from the multi-discipline of electronics, material science, electrochemistry, biochemistry, and immunochemistry. The technology of electroanalysis is an interplay between electricity and chemistry that concerns current, potential, and charge from a chemical reaction. There are two principal types of electroanalytical measurements, potentiometric and amperometric. Potentiometric technique is a static technique with no current flow; the established potential across the ion-select membrane is measured. With different types of membrane materials, the recognition of different ions can be reached. Thus, the potentiometric probes have been widely used for directly monitoring ionic species such as calcium, potassium, and fluoride ions. In amperometric technique, an electrode potential is used to drive an electron-transfer reaction. The responsive current is measured and related to the presence and/or concentration of the target analyte. In the past, potentiometric devices have been more widely applied in clinical chemistry laboratories. But with increasing amount of research on amperometric systems in diagnostics, the balance has shifted. The amperometric biosensors make possible a practical, fast, and routine measurement of test analytes. One trend of current biosensors focuses on the methodology of minimum demand of operator skills.

To date, most commercially used biosensors are amperometric ones that harness redox enzymes as recognizing biocomponents and electrodes as electrochemical transducers. The mass production of inexpensive and disposable devices has been achieved recently with the help of screen-printing technology. The success in the development of these devices has led to amperometric assays for several biomolecules including glucose, cholesterol, and various drugs. This type of amperometric biosensor is typically composed of an base member, two or three electrodes, an insulating layer, and a region for enzymatic reaction. Two-electrode biosensor consists of a working electrode, a counter electrode and a destined region where reagent for enzymatic reaction is placed. The reaction progresses when the sample liquid containing an analyte is applied onto the reaction area. Two physical effects, mesh spread and capillary action, are commonly used to guide a uniform distribution of the loaded sample on the reaction area. After the reaction is complete, the test analyte is oxidized and the electrons yielded from the reaction are trapped in a reduced co-product. A controlled-potential is then applied between the electrodes to trigger a second round of oxidoreduction. This electrical potential must be sufficient enough to drive a diffusion-limited electrooxidation at the surface of the working electrode, yet insufficient to activate irrelevant chemical reactions. After a time delay, the current produced by the electrochemical oxidoreduction is observed and measured and the current is correlated to the presence and/or amount of the analyte in the sample.

In the case of oxidation, oxygen is consumed in the oxidative reaction as a co-reactant and hydrogen peroxide is yielded as a co-product. The yield of hydrogen peroxide is proportional to the concentration of analyte. Hydrogen peroxide can be detected by oxidizing it at anodic potential (e.g., >0.6 V, Ag/AgCl) to generate an electrical signal (current). However, the potential required for oxidizing hydrogen peroxide can cause oxidation of other oxidizable chemicals such as ascorbate, bilirubin, uric acid, and the commonly used drug, e.g., acetaminophen, thus leading to an interference of electrical current to be detected. This interference can be avoided by replacing oxygen with an artificial mediator capable of transferring electrons from oxidoreductases. Several mediators have been used to enhance electron transfer between a variety of enzymes and electrodes, which include ferrocene and its derivatives, osmium complex, tetrathiofulvalene, phenazine ethosulfate, benzoquinone, and hexacyanoferrate.

Conventional methods of determining analytes in blood involves sample pretreatment. However, as pretreatment involves extra time and labor, these assays may benefit through the availability of a direct measurement of whole blood samples. More importantly, direct measurement of whole blood samples makes it possible for a real time monitoring for home users. For accurate measurement of a whole blood sample using an amperometric biosensor, a quick and homogenous reaction on the electrodes is essential for successful analyte determination. Reagents dried on a reaction area, including an oxidoreductase and a mediator, have to dissolve instantly when a small volume of sample blood is applied to the biosensor. These dissolved reagents must mix with the sample thoroughly for the completion of the enzymatic reaction and consistency of the subsequent electronic reaction.

The other common problems for assaying biological samples such as the whole blood are sample viscosity and the relatively large sample volume for the analysis. The whole blood sample, with its viscosity, might not be able to be distributed over sufficient reaction area. Moreover, viscosity and surface tension of samples may present a lag-time in sample introduction to the reaction area in biosensors, thus inhibiting real-time analysis of particular analytes. For some poorly bleeding people, it might be a problem to get enough blood from a prick on fingerstick. Three types of insufficient application of blood (or other viscous samples) have been observed: first, the sample covers only the front end of the test strip; secondly, the sample covers only the right half of the strip; and thirdly, the sample covers only the left half of the strip. The insufficient or non-homogenous application of sample fluid presents a lower amount of analyte, which causes an artificial and misleading result.

Moreover, with particular regard to glucose assays, current devices may only provide accurate results within a particular glucose range. This range may lie outside and below the range of particular diabetic patients which need a reliable indicator of blood glucose levels.

Another problem with current biosensors includes their instability at a range of temperatures, in that a difference in ambient temperature can alter the characteristics of the reaction area. This type of alteration may affect the speed of sample uptake into the device and overall accuracy due to incomplete loading of the sample.

Accordingly, there is a need in the art for biosensors and methods that provide for improved sample application and measuring properties. The present invention addresses this other related needs in the art.

BRIEF DESCRIPTION OF THE INVENTION

In one aspect, the present invention provides for a biosensor with which the sample fluid is distributed into a reaction area rapidly, uniformly and economically.

Sample fluid, e.g., blood, can be loaded by a punched hole on this sampling slot and can be drawn to the reaction area quickly facilitated by an outward surface tension provided by the arcuate portion of the sampling slot and a pull-up action provided by the reaction area. Furthermore, liquid soluble hydrophilic material positioned within the reaction area is utilized to enhance sample introduction and distribution. A homogenous distribution of sample fluid can be achieved and the test reagent works to trigger an reaction that starts the test.

In a frequent embodiment, a biosensor for electrochemical analysis of a liquid sample is provided, which biosensor comprises: a) a base member having a proximal and a distal end; b) a laminate member having a proximal and a distal end positioned in vertical, parallel alignment with said base member, wherein the laminate member defines a venting means and a sample application means positioned over said distal end of said laminate, and wherein said distal end of said laminate member is aligned with said distal end of said base member; c) an electrode system positioned between said base member and said laminate member, wherein said electrode system comprises a working electrode and a counter electrode, said working and counter electrodes having conductive leads at said proximal end of said base member for connecting said electrodes to a readout device for electrochemical measurement, wherein said working electrode is positioned adjacent to said counter electrode, and there is a gap space between said working and counter electrodes; d) an insulating layer positioned between said base member and said laminate member; e) a reaction area positioned between said base member and said laminate member, which reaction area encompasses at least a portion of said working electrode, said counter electrode and the gap space between said working electrode and said counter electrode, wherein the reaction area is defined by an opening between said base member and said laminate member, and which reaction area has a test reagent positioned therein; and f) a dielectric coating positioned between said electrode system and said base member and within at least a portion of the reaction area, wherein the test reagent comprises a liquid soluble hydrophilic component.

Frequently, the test reagent is positioned overlapping at least a portion of the working and counter electrodes, and wherein any portion of the test reagent not overlapping the working and counter electrodes is positioned on the insulating layer. Also frequently, the liquid soluble hydrophilic component comprises polyvinylpyridine (PVP). Also frequently, the biosensor further incorporates a dielectric coating positioned on the base member, wherein the dielectric coating is further positioned between said electrode system and said base member and within at least a portion of the reaction area. Often, the reaction area is further defined by a recess positioned in the laminate member between the sample application means and the venting means.

In a frequent embodiment, the reaction area comprises an opening or chamber in the biosensor having internal boundaries comprising the laminate member and the dielectric coating as opposing boundaries and a lateral boundary between the laminate member and the dielectric coating comprising the insulating layer together with a portion of the recess in the laminate member.

In another frequent embodiment, the working and counter electrodes are carbon coated. Frequently, the working and counter electrodes have two or more coatings of carbon at the portion encompassed by the reaction area. Also frequently, the working and counter electrodes are comprised mostly of silver paste, but are coated with carbon, except at the conductive leads. Also frequently, the working and/or counter electrodes are comprised mostly of silver paste, but comprise carbon within the reaction area, and are coated with carbon throughout, except at the conductive leads. Generally, the carbon is applied as carbon paste via a screen-printing method. Also generally, the silver is applied as a silver paste via a screen-printing method. Both the carbon paste and silver paste are dried on the device prior to incorporating additional components. Frequently, the reaction area comprises a complete cross-section of a portion of the electrode system. In another frequent embodiment, the working and counter electrodes are comprised of substantially identical material(s) within the reaction area. Also frequently, the gap space between the working electrode and the counter electrode is substantially constant within the reaction area.

In an occasional embodiment, the insulating layer and the dielectric coating are comprised of the same or different materials. Although frequently the insulating layer and the dielectric coating are comprised of the same material, but are incorporated as separate components of the present devices. Often the insulating layer and the dielectric coating are applied to the present devices at separate times and at separate locations. The dielectric coating is most frequently applied such that it lies within the reaction area such that test reagent, when applied to the device contacts the coating. Generally, the test reagent is dried over, or otherwise in contact with, at least a portion of the dielectric coating. In a frequent embodiment, the dielectric coating is positioned on the base member such that the portion of the working and counter electrodes positioned within the reaction area are positioned over, on top of, or otherwise contacting the dielectric coating. Thus, one side of the reaction area often comprises the dielectric coating together with the working and counter electrodes.

In one embodiment, the laminate member is comprised of polyurethane or polyethylene, and the adhesive is an acrylic-based adhesive. In a frequent embodiment, the base member comprises vinyl polymer(s), polymide(s), polyester(s), nylon, nitrocellulose or a combination thereof. On occasion, the base member and/or the laminate member is/are transparent; although the present description provides for and contemplates the base member and/or the laminate member, in addition to any of the other components of the present devices, as being colored, translucent, or otherwise detectably distinguishable components.

In another embodiment, the sample application means comprises one or more openings that allow fluid communication with the reaction area for sample application. Frequently, the one or more openings are positioned in the laminate member and provide for fluid communication from the outside with the reaction area. Also frequently, the one or more openings are positioned between the laminate member and the base member and provide for fluid communication from the outside with the reaction area. Thus, the sample application means frequently comprises a break, hole, opening, aperture, window or discontinuity in the laminate and/or dielectric layer that permits sample fluid to enter the reaction area.

Although frequently separately distinguished, a venting means may also be provided as a component of the sample application means. Generally, although not intending to be bound by theory, the venting means permits the evacuation of air, or other ambient gases, from the reaction area upon entry of sample fluid. Frequently, the venting means comprises one or more openings that allow evacuation of a gas from the reaction area upon sample application. Frequently, the one or more openings are positioned in the laminate member and provide for gaseous communication of the reaction area with the outside the device. Also frequently, the one or more openings are positioned between the laminate member and the base member and provide for gaseous communication of the reaction area with the outside the device. Thus, the venting means frequently comprises a break, hole, opening, aperture, window or discontinuity in the laminate and/or dielectric layer that permits the escape of a gas from the reaction area. Not intending to be bound by theory, the venting means may also, on occasion, permit escape of excess sample fluid.

In an occasional embodiment, the sample application means and the venting means are similarly situated such that their role in the device as venting means or sample application means is dependant on where the sample is applied. For example, if fluid sample is applied to one or more break(s), hole(s), opening(s), aperture(s), window(s) or discontinuities in the laminate and/or dielectric layer designed as a venting means or a sample application means, that one or more break(s), hole(s), opening(s), aperture(s), window(s) or discontinuities becomes a sample application means and the other aspect designed as a sample application means becomes a venting means. Also frequently, the sample application means and the venting means are positioned on the same side of the device. Although, when the sample application means and the venting means are positioned in the side of the present devices, on occasion, the sample application means and the venting means are positioned on different sides of the device. When either of the sample application means or the venting means are positioned on the side of the device, occasionally the other is positioned on/in the laminate member.

In another embodiment, the test reagent comprises a dried solution of a liquid soluble hydrophilic material, a surfactant and citric acid. Frequently, the liquid soluble hydrophilic material is comprised of PVP and the surfactant is comprised of Triton X-100. On occasion, an electron transfer mediator is disposed in the reaction area forming part of the test reagent. When incorporated in the present devices, the electron transfer mediator is often selected from the group consisting of ferrocene and its derivatives, osmium complex, tetrathiofulvalene, phenazine ethosulfate, benzoquinone and hexacyanoferrate.

In one aspect, the present invention provides for a biosensor by which the distribution of sample fluid can be ensured to cover all destined reaction area. The biosensor is of particular utility for use in an electrochemical sensor for measuring viscous sample fluids such as whole blood or samples containing large molecules.

In another aspect, the liquid soluble hydrophilic component is a material having hydrophilic properties deposited on or in the reaction area. Frequently, the liquid soluble hydrophilic component comprises PVP. In a frequent embodiment, the liquid soluble hydrophilic component, together with other unique aspects of the present devices, enables sample introduction, substantially uniform distribution within the reaction area, and a detectable result within about five seconds from the time the sample contacts the device. Also frequently, the liquid soluble hydrophilic component, together with other unique aspects of the present devices, enables sample entry and reaction time of less than one second.

In a frequent embodiment, the test reagent is comprised of between about 0.05% to about 2.0% liquid soluble hydrophilic component (e.g., PVP). Also frequently, the test reagent is comprised of about 0.5% liquid soluble hydrophilic component. On occasion, the test reagent is comprised of between about 0.05% to about 0.5% liquid soluble hydrophilic component. Also on occasion, the test reagent is comprised of between about 0.05% to about 1.5% liquid soluble hydrophilic component. Frequently, the test reagent is comprised of about 0.05%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.9%, about 0.95%, about 1.0%, about 1.1%, about 1.2%, about 1.3%, about 1.4%, about 1.5%, about 1.6%, about 1.7%, about 1.8%, about 1.9% or about 2.0%, or any of a variety of ranges therebetween of liquid soluble hydrophilic component. Frequently, the test reagent is further comprised of about 0.05% to about 2.0% surfactant material (e.g., Triton X-100). In a frequent embodiment, the test reagent is comprised of about 0.5% liquid soluble hydrophilic component and 0.5% surfactant. Moreover, the test reagent often further comprises citric acid. The citric acid component, is generally a buffered citric acid component comprising about 10 mM to about 1M, and preferably 100 mM. In a frequent embodiment, the constituent components of the test reagent are combined in solution and are deposited in the reaction area in a liquid, gel, solid, powdered, aerosolized or gaseous form. Also frequently, the components of the test reagent are combined in a buffered solution and deposited and dried in the reaction area. Often the test reagent is dispensed within the reaction area via a pump or screen-printing means.

On occasion, the test reagent further comprises an enzyme that catalyzes a reaction involving an analyte to be analyzed (e.g., glucose oxidase). The reaction of a particular analyte and such reaction components generally produces a measurable electric potential between the working and reference electrodes.

In another embodiment, a method is provided for assaying an analyte or an enzyme in a liquid sample, which method comprises: contacting a liquid sample containing or suspected of containing an analyte with the sample application means of a presently described biosensor under suitable conditions whereby an electric potential is generated; and detecting the generated electric potential, whereby the presence or amount of the analyte or enzyme in the sample liquid is assessed.

In a frequent embodiment, the volume of the liquid sample contacted with the biosensor and necessary to produce a reading is a small amount. Frequently, the volume of the liquid sample contacted with the biosensor ranges between about 1.0 microliter and about 3.0 microliters. Also frequently, the volume of the liquid sample contacted with the biosensor is more than about 1.0 microliter, but wherein the volume of sample the enters the reaction area is between about 1.0 microliter to about 3.0 microliters. Thus, a larger sample may be contacted with the device, but frequently only a portion of the larger sample enters the reaction area.

In another embodiment, the analyte to be detected is glucose. When the analyte to be detected is glucose, frequently the glucose level in the sample is between about 20 mg/dL to about 600 mg/dL. On occasion, the glucose level in the sample is between about 300 mg/dL to about 600 mg/dL.

A method of manufacturing the presently described devices is also contemplated. In one embodiment, such a method comprises: applying the dielectric coating to the base member; applying the electrode system to the base member and over a portion of the dielectric coating; applying the insulating layer to the base member and over at least a portion of the electrode system but not within the reaction area; applying the test reagent to at least a portion of the dielectric coating within the reaction area; and adhering the laminate member to the insulating layer. Frequently, the dielectric coating, the electrode system and/or the insulating layer are applied via a screen-printing method.

DETAILED DESCRIPTION OF THE INVENTION

Figure 1:
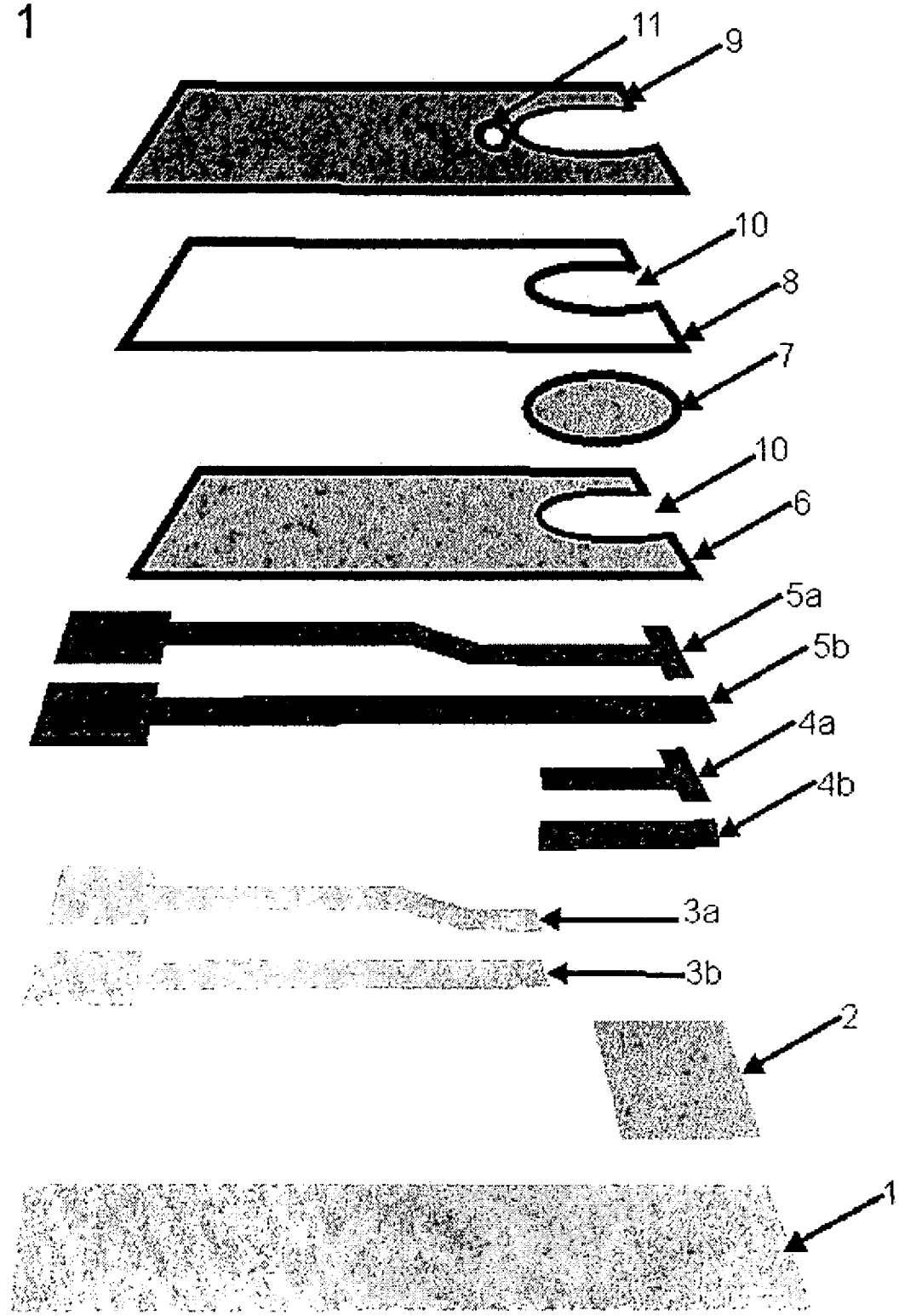
FIG. 1 depicts an exploded view of a preferred embodiment of an example test strip.

In one embodiment, the present invention provides for a device with which applied sample fluid is distributed into a reaction area rapidly, uniformly and economically. Sample fluid, e.g., blood, can be loaded by a sample application means and is drawn to the reaction area quickly, facilitated by an outward surface tension, pull-up action provided by the reaction area, the venting means and the liquid soluble hydrophilic component of the test reagent. A homogenous distribution of sample fluid can be achieved and the test reagent works to trigger an reaction that starts a test.

Problems surrounding the use of whole blood in biosensor-type assays have also included temperature fluctuations, contamination by other blood components, high concentrations of blood components and general lag-time of blood entering a device and providing an adequate and accurate reaction. U.S. Pat. Nos. 5,708,247 and 5,951,836 attempted to overcome some of these problems through the use of a screen printed coating on the electrodes of a biosensor device. This was an insoluble coating comprised of silica and contained hydrophilic and hydrophobic portions which swells upon introduction of sample. Devices of these patents also utilize a polyester mesh to cover the reaction area in order to guide sample to a reference electrode.

In U.S. Pat. No. 6,241,862 a similar insoluble screen printed silica-based filler is used. The silica-based filler has both hydrophobic and hydrophilic components and works to exclude red blood cells and thereby render the device insensitive to the hematocrit of the sample. This insoluble coating swells upon introduction of liquid sample. Devices of this patent also utilize a polyester mesh to cover the reaction area in order to guide sample to a reference electrode.

U.S. Pat. No. 5,997,817 utilized a particular coating in a test chamber of a device and notches in a sample application port to purportedly reduce "dose hesitation," in addition to a "fill to here" line to gauge when sufficient sample entered the test chamber. The coating is described as consisting of polyethylene oxide having a particular molecular weight within a particular concentration.

U.S. Pat. No. 5,628,890 utilized insoluble surfactant coated mesh layers in an attempt to guide a liquid sample from the working to reference electrodes and ensure adequate sample has been introduced to produce an accurate result.

Definitions

Unless defined otherwise, all technical and scientific terms used herein have the same meaning as is commonly understood by one of ordinary skill in the art to which this invention belongs. All patents, applications, published applications, other publications and databases referred to herein are incorporated by reference in their entirety. If a definition set forth in this section is contrary to or otherwise inconsistent with a definition set forth in applications, published applications and other publications that are herein incorporated by reference, the definition set forth in this section prevails over the definition that is incorporated herein by reference.

As used herein, "a" or "an" means "at least one" or "one or more."

As used herein, "a direction perpendicular to said conductive leads" refers to a direction which is substantially non-opposing or substantially nonlinear to the direction of the conductive leads. Ordinarily, the angle between the direction perpendicular to the conductive leads and the direction of the conductive leads is from about 45 degrees to about 135 degrees. Preferably, the angle between the two directions is from about 80 degrees to about 100 degrees. More preferably, the angle between the two directions is from about 85 degrees to about 95 degrees. Most preferably, the angle between the two directions is about, or is, 90 degrees.

As used herein, "a direction parallel to said conductive leads" refers to a direction which is substantially opposing or linear to the direction of the conductive leads. Ordinarily, the angle between the direction parallel to the conductive leads and the direction of the conductive leads is about 0–45 degrees or 135–180 degrees. Preferably, the angle between the two directions is about 0–10 degrees or 170–180 degrees. More preferably, the angle between the two directions is 0–5 degrees or 175–180 degrees. Most preferably, the angle between the two directions is about, or is, 0 or 180 degrees.

As used herein, an "enzyme that catalyzes a reaction involving an analyte to be analyzed" refers to an enzyme that directly or indirectly oxidizes or reduces the analyte to be analyzed whereby the oxidization or reduction, in conjunction with an electron transfer mediator either as part of the biosensor or is added during the assay, leads to the generation of a current that is capable of being detected. Preferably, the enzyme uses the analyte as an immediate substrate in its catalyzed oxidizing or reducing reaction. For example, if the analyte to be analyzed is glucose, the enzyme can be an glucose oxidase.

As used herein, a "substrate that is involved in a reaction catalyzed by an enzyme of interest" refers to a substrate that is directly or indirectly used in an oxidizing or reducing reaction catalyzed by an enzyme to be analyzed whereby the oxidization or reduction, in conjunction with an electron transfer mediator either as part of the biosensor or is added during the assay, leads to the generation of a current that is capable of being detected. Preferably, the substrate is as an immediate substrate in the oxidizing or reducing reaction catalyzed by an enzyme to be analyzed. For example, if the enzyme to be analyzed is a glucose oxidase, the substrate can be glucose.

As used herein, "working and counter electrodes are made of substantially identical material(s)" means that identical or nearly identical material(s) are used in both working and counter electrodes so that both electrodes have identical or nearly identical electron transfer properties. Ordinarily, the difference of the electron transfer properties between the two electrodes is less than 50%. Preferably, the difference of the electron transfer properties between the two electrodes is less than 10%. More preferably, the difference of the electron transfer properties between the two electrodes is less than 1%. Most preferably, the working and counter electrodes are made of identical material(s) and there is no difference in their electron transfer properties.

As used herein, "the gap space between the working electrode and the counter electrode is kept substantially constant" means that difference of the gap space between the working electrode and the counter electrode is sufficiently small so that when the working and counter electrodes are made of substantially identical material(s) and have substantially identical surface area, the difference of the gap space between the working electrode and the counter electrode, if there is any, would not affect the uniformity of the electrode performance. Ordinarily, the difference of the gap space between the working electrode and the counter electrode is less than 50%. Preferably, the difference of the gap space is less than 10%. More preferably, the difference of the gap space is less than 1%. Most preferably, the gap space between the working electrode and the counter electrode is kept constant.

As used herein, "the surface area of the working electrode is substantially identical to the surface area of the counter electrode" means that the difference of the surface area between the working electrode and the counter electrode is sufficiently small so that when the working and counter electrodes are made of substantially identical material(s) and the gap space between the working electrode and the counter electrode is kept substantially constant, the difference of the surface area between the working electrode and the counter electrode, if there is any, would not affect the uniformity of the electrode performance. Ordinarily, the difference of the surface area between the working electrode and the counter electrode is less than 50%. Preferably, the difference of the surface area is less than 10%. More preferably, the difference of the surface area is less than 1%. Most preferably, the surface area of the working electrode is identical to the surface area of the counter electrode.

As used herein, "working, counter and reference electrodes are made of substantially identical material(s)" means that identical or nearly identical material(s) are used in working, counter and reference electrodes so that the electrodes have identical or nearly identical electron transfer properties. Ordinarily, the difference of the electron transfer properties among the electrodes is less than 50%. Preferably, the difference of the electron transfer properties among the electrodes is less than 10%. More preferably, the difference of the electron transfer properties among the electrodes is less than 1%. Most preferably, the working, counter and reference electrodes are made of identical material(s) and there is no difference in their electron transfer properties.

As used herein, "the gap space between the reference electrodes and the working or counter electrode is kept substantially constant" means that difference of the gap space between the reference electrodes and the working or counter electrode is sufficiently small so that when the working, counter and reference electrodes are made of substantially identical material(s) and the working and counter electrodes have substantially identical surface area, the difference of the gap space between the reference electrodes and the working or counter electrode, if there is any, would not affect the uniformity of the electrode performance. Ordinarily, the difference of the gap space between the reference electrodes and the working or counter electrode is less than 50%. Preferably, the difference of the gap space is less than 10%. More preferably, the difference of the gap space is less than 1%. Most preferably, the gap space between the reference electrodes and the working or counter electrode is kept constant.

As used herein the term "assessing (or assessed)" is intended to include quantitative and qualitative determination in the sense of obtaining an absolute value for the amount or concentration of the analyte or enzyme, e.g., a protein or nucleic acid, present in the sample, and also of obtaining an index, ratio, percentage, visual or other value indicative of the level of analyte or enzyme in the sample. Assessment may be direct or indirect and the chemical species actually detected need not of course be the analyte or enzyme itself but may for example be a derivative thereof or some further substance.

As used herein the term "hydrophilic" refers to having an affinity for, attracting, adsorbing, associating with, or absorbing water molecules. Generally, hydrophilic refers to a material possessed by polar radicals or ions.

As used herein the term "hydrophilic means" or "hydrophilic material" refer to a liquid soluble material having hydrophilic properties. For example, the hydrophilic means may comprise, in part, a soluble hydrophilic material such as polyvinylpyridine (PVP). The hydrophilic means may further comprise additional elements such as a surfactant such as Triton X-100 and citric acid. The hydrophilic material and the surfactant may each comprise about 0.05% to about 2.0% of the entire hydrophilic solution mixture. Frequently the hydrophilic means is comprised of about 0.5% hydrophilic material and 0.5% surfactant. The citric acid component may frequently comprise about 10 mM to about 1M, and preferably 100 mM. In one aspect the constituent parts of the hydrophilic means are mixed in solution and are deposited in the reaction area in a liquid, gel, solid, powdered, aerosolized or gaseous form. Frequently, the components of the hydrophilic means are combined in a buffered citric acid solution and deposited and dried in the reaction area. The hydrophilic means may also be combined with an enzyme that catalyzes a reaction involving an analyte to be analyzed to provide a reaction component.

Hydrophilic means of the present invention generally become soluble in a liquid sample (e.g., blood) upon contact therewith. As the preferred hydrophilic means are liquid-soluble, preferred hydrophilic means do not detrimentally affect any intended reaction of an analyte of interest with enzymes or other reaction components positioned in test strips of the present invention. Therefore, hydrophilic means are provided to enhance sample entry and distribution within test strips of the present invention, and have only a neutral or beneficial effect on any intended reaction of an analyte of interest in the presently described test strips.

As used herein, "macromolecule" refers to a molecule that, without attaching to another molecule, is capable of generating an antibody that specifically binds to the macromolecule.

As used herein, "small molecule" refers to a molecule that, without forming homo-aggregates or without attaching to a macromolecule or adjuvant, is incapable of generating an antibody that specifically binds to the small molecule. Preferably, the small molecule has a molecular weight that is about or less than 10,000 Daltons. More preferably, the small molecule has a molecular weight that is about or less than 5,000 Daltons.

As used herein, "vitamin" refers to a trace organic substance required in certain biological species. Most vitamins function as components of certain coenzymes.

As used herein, "lipid" refers to water-insoluble, oily or greasy organic substances that are extractable from cells and tissues by nonpolar solvents, such as chloroform or ether.

As used herein, a "receptor" refers to a molecule that has an affinity for a given ligand. Receptors may be naturally-occurring or synthetic molecules. Receptors may also be referred to in the art as anti-ligands. As used herein, the receptor and anti-ligand are interchangeable. Receptors can be used in their unaltered state or as aggregates with other species. Receptors may be attached, covalently or noncovalently, or in physical contact with, to a binding member, either directly or indirectly via a specific binding substance or linker. Examples of receptors, include, but are not limited to: antibodies, cell membrane receptors surface receptors and internalizing receptors, monoclonal antibodies and antisera reactive with specific antigenic determinants such as on viruses, cells, or other materials, drugs, polynucleotides, nucleic acids, peptides, cofactors, lectins, sugars, polysaccharides, cells, cellular membranes, and organelles.

As used herein, "antibody" includes antibody fragments, such as Fab fragments, which are composed of a light chain and the variable region of a heavy chain. Antibody encompasses polyclonal and monoclonal antibody.

As used herein, "nutrient or storage protein" refers to a protein that is used by the cell as the nutrient source or storage form for such nutrient. Non-limiting examples of nutrient or storage proteins include gliadin, ovalbumin, casein, and ferritin.

As used herein, "contractile or motile protein" refers to a protein that endows cells and organisms with the ability to contract, to change shape, or to move about. Non-limiting examples of contractile or motile proteins include actin, myosin, tubulin and dynein.

As used herein, "structural protein" refers to a protein that serves as supporting filaments, cables, or sheets to give biological structures strength or protection. Non-limiting examples of structural proteins include keratin, fibroin, collagen, elastin and proteoglycans.

As used herein, "defense protein" refers to a protein that defends organisms against invasion by other species or protect them from injury. Non-limiting examples of defense proteins include antibodies, fibrinogen, thrombin, botulinus toxin, diphtheria toxin, snake venoms and ricin.

As used herein, "regulatory protein" refers to a protein that helps regulate cellular or physiological activity. Non-limiting examples of regulatory proteins include insulin, growth hormones, corticotropin and repressors.

As used herein, "sample" refers to anything which may contain an analyte or enzyme for which an analyte or enzymatic assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). The sample may also be a mixture of target analyte or enzyme containing molecules prepared in vitro.

As used herein, a "liquid sample" or "fluid sample" refers to a sample that naturally exists as a liquid or fluid, e.g., a biological fluid. A "liquid sample" also refers to a sample that naturally exists in a non-liquid status, e.g., solid or gas, but is prepared as a liquid, fluid, solution or suspension containing the solid or gas sample material. For example, a liquid sample can encompass a liquid, fluid, solution or suspension containing a biological tissue.

As used herein, "tissue" refers to a collection of similar cells and the intracellular substances surrounding them. There are four basic tissues in the body: 1) epithelium; 2) connective tissues, including blood, bone, and cartilage; 3) muscle tissue; and 4) nerve tissue.

As used herein, "animal" refers to a multi-cellular organism of the kingdom of Animalia, characterized by a capacity for locomotion, nonphotosynthetic metabolism, pronounced response to stimuli, restricted growth and fixed bodily structure. Non-limiting examples of animals include birds such as chickens, vertebrates such fish and mammals such as mice, rats, rabbits, cats, dogs, pigs, cows, ox, sheep, goats, horses, monkeys and other non-human primates.

As used herein, "disease or disorder" refers to a pathological condition in an organism resulting from, e.g., infection or genetic defect, and characterized by identifiable symptoms.

For clarity of disclosure, and not by way of limitation, the detailed description of the invention is divided into the subsections that follow.

Biosensors Containing a Sample and Reaction Area and Methods Using the Same

In one embodiment, a biosensor is provided for electrochemical analysis of a liquid sample, which biosensor comprises: a base member having a proximal and a distal end; a laminate member having a proximal and a distal end positioned in vertical, parallel alignment with said base member, wherein the laminate member defines a venting means and a sample application means positioned over said distal end of said laminate, and wherein said distal end of said laminate member is aligned with said distal end of said base member; an electrode system positioned between said base member and said laminate member, wherein said electrode system comprises a working electrode and a counter electrode, said working and counter electrodes having conductive leads at said proximal end of said base member for connecting said electrodes to a readout device for electrochemical measurement, wherein said working electrode is positioned adjacent to said counter electrode, and there is a gap space between said working and counter electrodes; an insulating layer positioned between said base member and said laminate member; and a reaction area positioned between said base member and said laminate member and near said distal end of said base member and said laminate member, which reaction area encompasses at least a portion of said working electrode, said counter electrode and the gap space between said working electrode and said counter electrode, wherein the reaction area is defined by an opening between said base member and said laminate member, and which reaction area has a test reagent positioned therein, wherein the test reagent comprises a liquid soluble hydrophilic component. Often, the reaction area is further defined by a recess positioned in the laminate member between the sample application means and the venting means. Frequently, the liquid soluble hydrophilic component comprises polyvinylpyridine (PVP). Also frequently, the biosensor further incorporates a dielectric coating positioned on the base member, wherein the dielectric coating is further positioned between said electrode system and said base member and within at least a portion of the reaction area. Frequently, the dielectric coating is positioned between said electrode system and said base member and within at least a portion of the reaction area. Also frequently, the test reagent is positioned overlapping at least a portion of the working and counter electrodes, and wherein the portion of the test reagent not overlapping the working and counter electrodes is positioned on the insulating layer.

Although particular configurations are described and depicted herein, an exemplary biosensor can be configured in any suitable shape.

Moreover, the base member can be comprised of any suitable material(s). Frequently, the base member comprises vinyl polymer(s), polymide(s), polyester(s), nylon, nitrocellulose or a combination thereof. Generally, base members of the present description are rigid, semi-rigid or flexible in that they may act to structurally support the biosensor. Frequently, the base member acts to support the biosensor while inserted into a readout device, before, during and/or after sample application.

The working and counter electrodes can be comprised of any suitable material(s). Although not required, the working and counter electrodes are preferably comprised of substantially similar material(s) within the reaction area. More preferably, the working and counter electrodes are comprised of identical material(s) within the reaction area. Most preferably, the working and counter electrodes are comprised of identical material(s) throughout the entire biosensor. However, on occasion, the working and counter electrodes are comprised of different material(s), each having similar or comparable electric conductive characteristics throughout the entire biosensor and/or within the reaction area.

The gap space between the working electrode and the counter electrode can be kept constant or may vary. Frequently, the gap space between the working electrode and the counter electrode is kept substantially constant within the reaction area. Also frequently, the gap space between the working electrode and the counter electrode is kept constant within the reaction area. On occasion, the gap space between the working electrode and the counter electrode is kept constant throughout the entire biosensor.

The width of the working electrode can be identical to or different from the width of the counter electrode within the reaction area. In a frequent embodiment, the width of the working electrode is about twice of the width of the counter electrode within the reaction area. Nevertheless, a variety of widths and configurations are within the scope of the present disclosure.

The surface area of the working electrode can be identical to or different from the surface area of the counter electrode. Frequently, the surface area of the working electrode is substantially identical to the surface area of the counter electrode within the reaction area. Also frequently, the surface area of the working electrode is identical to the surface area of the counter electrode within the reaction area. On occasion, the surface area of the working electrode is identical to the surface area of the counter electrode throughout the entire biosensor.

In a frequent embodiment, the working and counter electrodes are comprised of identical material(s) within the reaction area, and the gap space between the working electrode and the counter electrode is kept constant within the reaction area.

The electrode system can be placed or disposed on the base member and/or the dielectric coating by any suitable methods known in the art. For example, electrodes can be unrolled from reels and attached to the base member using hot melt adhesive. Frequently, the electrode system is screen-printed onto the base member. When the electrode system is screen-printed onto the base member, the working and counter electrodes can comprise carbon paste and the conductive leads can comprise conductive silver paste. The electrode system can also be placed or made onto the base member by a variety of methods, including, for example, those disclosed in the following references: Kureishi et al., *Bioelectrochem. Bioenerg.*, 48(1):95–100 (1999); Anzai et al., *Anal. Chem.*, 70(4):811–7 (1998); and Stonehuerner et al., *Biosens. Bioelectron.*, 7(6):421–8 (1992).

In a frequent embodiment, the electrode system is thicker in the area comprised in the reaction area. The thickness of the electrodes is often due to the incorporation of multiple layers of the material forming the electrode in the reaction area such as carbon. Thus, two or more layers of electrode material is often incorporated in the reaction area. It was surprisingly recognized in leading to the present disclosure that an increased thickness of the electrode in the area comprising the reaction area provides more surface area and enhances the ability to measure analyte, if present, in the sample. The extra layer, if utilized, is generally positioned within the area subsequently forming the reaction area via the same or similar means utilized to position the initial electrode system. Alternatively, a layer of electrode system material can be positioned in the area subsequently forming the reaction area, followed by the positioning of the entire electrode system on top of this initial layer and across the entire device, thereby forming a thicker electrode component in the reaction area.

The reaction area can be defined by covering the non-reaction-area with an insulating layer often comprising a dielectric material. In addition, or independently, a dielectric coating is frequently positioned in at least a portion of the reaction area. Any suitable dielectric material can be used. Preferably, the dielectric material used in the biosensor is vinylpolyester(s), polyimide(s) or a combination thereof. Tables 1 and 2 set out exemplary dielectric material compositions available from Acheson Colloids Co., Port Huron, Ill.

Frequently, the dielectric material is applied or positioned on the device between the laminate member and the base member. More particularly, often the dielectric material is positioned or applied between the laminate member and the base member and over at least a portion of the electrode system. The dielectric material often will comprise the intermediate material between the laminate member and the base member, including the electrode system. On occasion, the dielectric material is absent from the reaction area. Frequently, however, the dielectric material forms one or more lateral internal boundaries of the reaction area within the device. For example, the dielectric material often can comprise the lateral boundary for the reaction area on all sides when the sample application means and venting means are positioned on or in the laminate or base members. In another example, the dielectric material forms a lateral boundary for the reaction area, but includes a break for the sample application and/or venting means. On occasion, the laminate member can be lined with a dielectric material such that the dielectric material positioned on the laminate member comprises the upper portion or boundary of the reaction area.

TABLE 1

| Ingredients | % Composition |
|---|---|
| Methacrylate Grafted Polybutadiene | 15–40 |
| Acrylate/Methacrylate Resin | 1–5 |
| Dicyclopentenyloxyethyl Acrylate | 15–40 |
| 2-Hydroxy-2methyl-1-phenyl-1-propanone | 1–5 |
| Polydimethylsiloxane/Silica Adduct | 1–5 |
| Talc (Hydrous magnesium silicate) | 10–30 |

TABLE 2

| Ingredients | % Composition |
|---|---|
| 1, 6 Hexanediol Diacrylate | 1–5 |
| Proprietary Acrylate Oligomer | 10–30 |
| Proprietary HMIRC# 5500 | 1–5 |
| Dicyclopentenyloxyethyl Acrylate | 15–40 |
| Proprietary Photoinitiator | 1–5 |
| Polydimethylsiloxane/Silica Adduct | 1–5 |
| Talc (Hydrous magnesium silicate) | 10–30 |
| Proprietary ingredient | .05–1.5 |

In a frequent embodiment, a preferred hydrophilic component comprises polyvinylpyridine ("PVP"). Also frequently, the hydrophilic material comprises a material having a molecular weight between about 10,000 and 360,000, and preferably has a molecular weight of about 10,000. Although not intending to be bound by theory, other molecular weights below and above these ranges may be acceptable. Moreover, the intrinsic viscosity of the hydrophilic component generally lies between K=12 and K=100, with a preferred intrinsic viscosity of between about K=12 to K=18. Although not intending to be bound by theory, other intrinsic viscosity's below and above these ranges may be acceptable.

In a particularly frequent embodiment, a dielectric coating is further included in the test device. The insulating layer and the dielectric coating are often comprised of the same materials, but constitute distinguishable components of the present devices and methods. Thus, the insulating layer and the dielectric coating are often comprised of the same material, and are also incorporated as separate components of the present devices. As such, the insulating layer and the dielectric coating are often configured in the present devices at separate times and at separate locations.

The dielectric coating is most frequently applied in a position that lies within the reaction area such that a test reagent, when applied to the device, contacts the coating. Generally, the test reagent is dried over, or otherwise in contact with, at least a portion of the dielectric coating. In a frequent embodiment, the dielectric coating is positioned on the base member such that the portion of the working and counter electrodes positioned within the reaction area are positioned over, on top of, or otherwise contacting the dielectric coating. Thus, one side of the reaction area often comprises the dielectric coating together with the working and counter electrodes. Although not necessarily co-extensive, the overlap of the test reagent with the dielectric coating is frequently of a degree that the test reagent does not directly contact the base layer. In such an embodiment, the test reagent is deposited on the device over a portion of the electrode system and the dielectric coating. See, e.g., FIG. 1.

Figure 3:
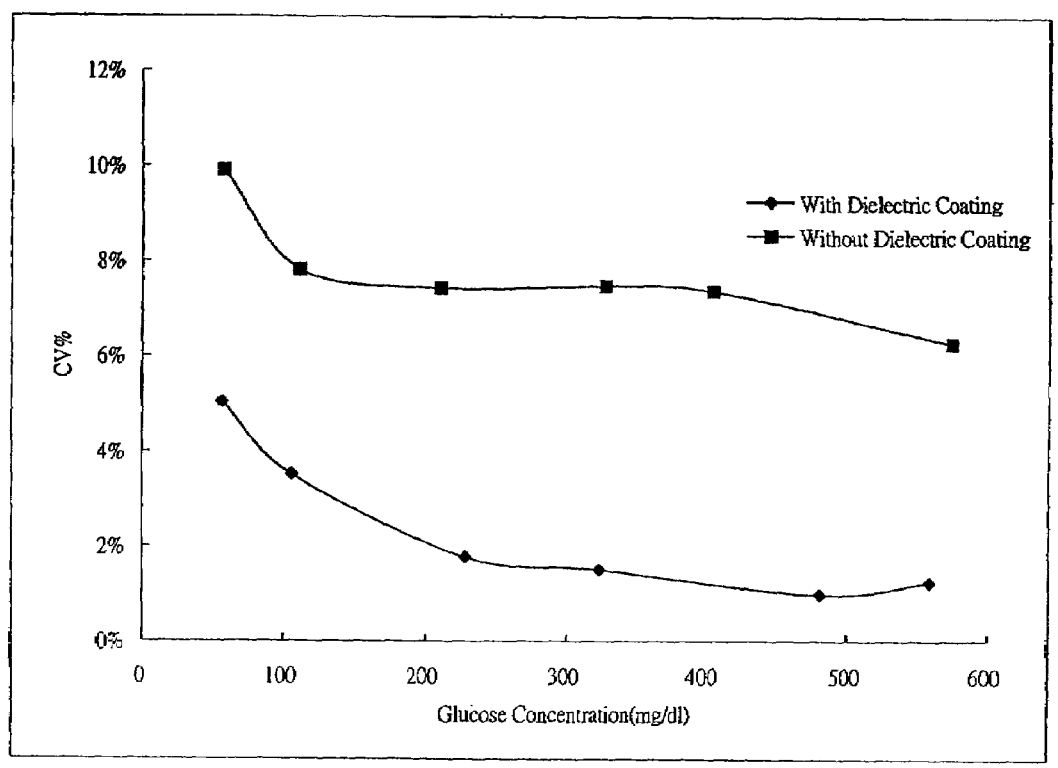
FIG. 3 provides a graph depiction of the effect of the coefficient of variation (CV) at a given glucose level on the electrode response by a control test strip that lacks a dielectric coating material (squares) and a test strip having a dielectric coating in accordance with the present description (diamonds).

In leading to the present disclosure it was recognized that manufacturing processes frequently subject test devices (or sheets comprising multiple devices) to various mechanical forces. These forces are often visited on incomplete devices, during necessary steps of their manufacture (e.g., punching holes, sectioning sheets comprising multiple devices, etc.). Such forces often lead to the breakage or dislodging of a test reagent dried on/in the device. This breakage generally comprises of a loosening of the dried test reagent such that it is not in optimal positioning for conducting an assay. Often the breakage comprises dislodging of dried reagent from a first dried position within the reaction area, or in a region that will comprise the reaction area upon complete device assembly. In leading to the present disclosure it was discovered that positioning of a dielectric coating within the reaction zone in a manner such that the test reagent is dried on this dielectric coating will provide a stronger bond with the test reagent. This stronger bond fixes the test reagent within the reaction area, despite the application of manufacturing related mechanical forces. Moreover, the use of the dielectric coating as a surface for the deposit of the test reagent protects the present devices from other, post-manufacture, physical forces. These types of forces may occur during shipping, storage, transport or use. In a frequent embodiment, the inclusion of a dielectric coating in a device of the present description improves the overall performance of the device, regardless of whether it is exposed to physical trauma. Other benefits of the inclusion of the dielectric coating are contemplated. FIG. 3 provides a graph depiction of the effect of the CV % at a given glucose level on the electrode response by a control test strip that lacks a dielectric coating material (squares) and a test strip having a dielectric coating in accordance with the present description (diamonds). As indicated in FIG. 3, the dielectric coating provides for assay results having a lower CV % across the board (versus devices without the dielectric coating), with the variability averaging well below 4%, and generally below 2%, over a large glucose concentration range.

Figure 4:
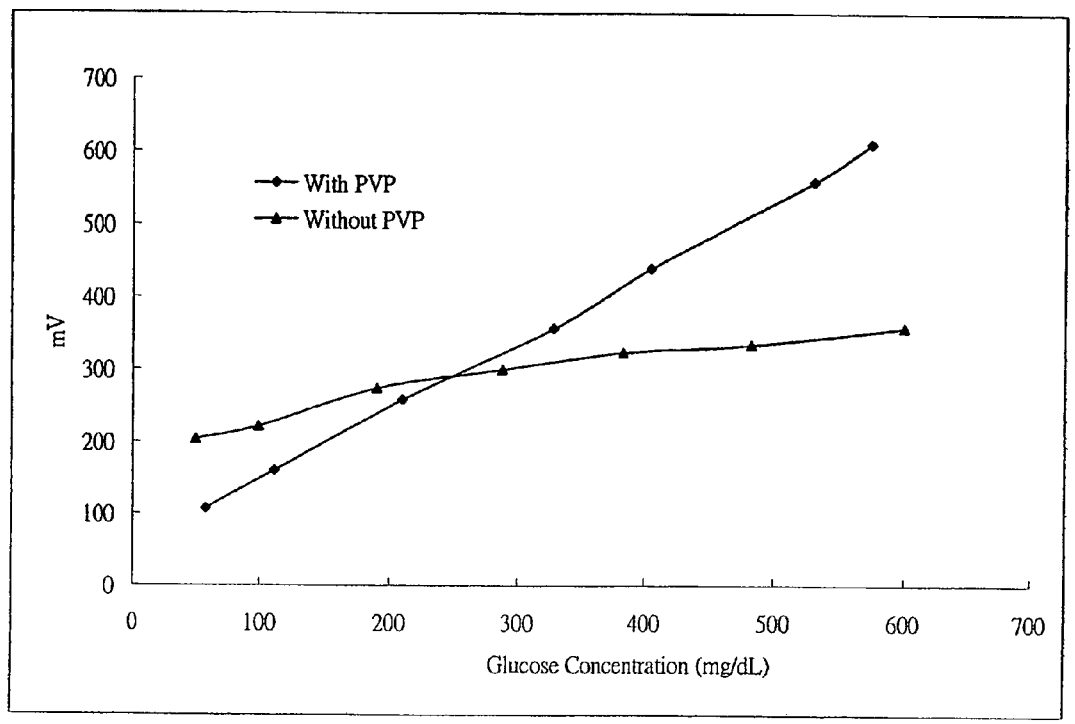
FIG. 4 provides a graph depiction of the effect of a given glucose level on the electrode response in a control test strip that lacks a liquid soluble hydrophilic reagent (triangles) and a test strip having a liquid soluble hydrophilic reagent in accordance with the present description (diamonds).

In a particularly frequent embodiment, the hydrophilic component is soluble in liquid. Often, the hydrophilic component readily dissolves in a sample solution. A variety of sample types are contemplated herein and the hydrophilic component frequently readily dissolves in samples such as blood samples upon contact with these liquid or fluid samples. Moreover, not only the hydrophilic component, but the entire test reagent frequently is soluble in liquid. Although many samples may have a medium to high viscosity, the present hydrophilic component(s) and/or the entire test reagent frequently is/are readily soluble in these samples. In contrast to method and devices whereby an insoluble hydrophilic material is used, the present test reagents and hydrophilic materials readily dissolve in fluid samples. Furthermore, the present test reagents and hydrophilic components generally do not interfere with the reaction necessary to produce a detectable electric potential in the present devices. In contrast, the present test reagents and hydrophilic components often enhance the reaction necessary to produce a measurable electric potential if an analyte of interest is present in the sample within detectable levels. For example, see FIG. 4 which provides a graph depiction of the effect of a given glucose level on the electrode response (in mV) in a control test strip that lacks a liquid soluble hydrophilic reagent (triangles) and a test strip having a liquid soluble hydrophilic reagent in accordance with the present description (diamonds). The electrode response is markedly increased in mid to higher glucose concentrations.

As indicated, the hydrophilic component is frequently combined with other materials and/or reagents to produce a combined test reagent. This reagent can be in liquid or gel form, or may be dried and prepared for reconstitution. Frequently, the hydrophilic component is combined with a surfactant and a solution of citric acid to produce a hydrophilic test reagent. Furthermore, the test reagent is generally positioned and dried on or in the device for use of the device. Frequently the presently contemplated test reagent components are be combined in exemplary test reagent compositions as set out below in Tables 3 and 4, although other compositions and mixtures are contemplated.

TABLE 3

| Component | Composition |
| --- | --- |
| Hydrophilic material (e.g., Polyvinylpyridine) | 0.05%–2.00% |
| Surfactant (e.g., Triton X-100) | 0.05%–2.00% |
| Citric Acid | 10 mM–100 mM |

TABLE 4

| Component | Composition |
| --- | --- |
| Hydrophilic material (e.g., Polyvinylpyridine) | 0.5% |
| Surfactant (e.g., Triton X-100) | 0.5% |
| Citric Acid | 100 mM |

It was surprisingly recognized in leading to the present disclosure that the positioning of the test reagent over a layer of dielectric material enhances the resultant reactivity of the device. Such positioning is generally over the dielectric coating and the electrode system as the test reagent generally contacts the electrode system directly in an unused device. The positioning of the test reagent over the dielectric coating material often enhances the affinity with which the test reagent is positioned in the reaction area while avoiding the inhibition of the reaction of the test reagent with the sample. Frequently, the dielectric coating material, or means for positioning the test reagent, avoids inhibition of the intended reaction of the sample within the reaction area. Although not bound by any particular theory, the test reagent may become brittle subsequent to positioning within the reaction area and thereby come loose prematurely prior to use of the device.

As indicated herein, the use of a means such as the present dielectric materials within the reaction area enhances the ability to accurately and reliably position the test reagent within the reaction area. In one embodiment, a material such as the present dielectric material is positioned within the reaction area to enhance the affinity with which the test reagent is positioned in the reaction area.

The top layer of the presently described devices may be formulated with a unique laminate member. In frequent embodiments this top layer is comprised of an adhesive material together with a laminate. Together these two components often form one contiguous top layer. In one particular embodiment, a double sided adhesive tape is utilized to secure the top layer to the lower layer(s) (comprising the base member, dielectric material and electrode system). In a frequent embodiment of the present devices, the adhesive layer comprises a double sided tape (Tape 9824) produced by Minnesota Mining and Manufacturing Company, Engineering Adhesives Division, 3M Center, Building 551-2W-02, St. Paul, Minn. 55144 ("3M©"). An exemplary tape comprises polyurethane tape No. 9824, including adhesive No. 340. Tapes such as 3M's© Tape #9824 are beneficial for the present invention as they are generally not affected by temperature; thus, the adhesive properties remain as does the consistency of the channel height regardless of changes in ambient temperature. Moreover, the structure of these particularly preferred tapes allows for uniform channel formation as well as ease of manufacture. Product specific characteristics of particularly preferred tapes can be obtained directly from 3M©.

The laminate frequently covers the entire reaction area. Also frequently, the biosensor incorporates a laminate that covers the surface of the majority of the biosensor, including the top of the reaction area. Often this laminate spans from the proximal to the distal end of the device, with the exception of the conductive leads. In one example, the laminate for the entire biosensor is a lamina adhered to the non-reaction-area and the opening on the top comprises a punched hole formed on the lamina. On occasion, the punched hole of the lamina includes an arcuate component of the sampling slot protruding into the reaction area to form a convex, said convex serves as the passage for the sample fluid to the reaction area and the arcuate part of the convex provides an auxiliary of propulsion for a quick draw of the sample fluid. Frequently the venting means enhances sample entry into the reaction area.

The laminate member is often positioned or adhered to the insulating layer. In a frequent embodiment, the laminate member is positioned or adhered to the material forming the insulating layer and forms the upper boundary of the reaction area. The laminate member can be comprised of a variety of materials, but generally comprises a polymer such as polyester (i.e., Mylar), or other plastics or polymers known in the art.

The laminate member often is comprised of multiple discreet layers. For example, the laminate member may comprise a top Mylar layer together with another Mylar layer adhered to the top layer. This other Mylar layer often incorporates a recess in the area which will form or forms the reaction area. The recessed area permits the configuration of a larger and consistent reaction area or chamber. Alternatively, this other Mylar layer is discontinuous in the area which will form or forms the reaction area, thereby forming a recess within the laminate member as a whole within the area which will form or forms the reaction area. In another embodiment, this other layer comprises a material other than the same material forming the top layer, such as a dielectric material. On occasion, however, the laminate member comprises a single material which may or may not incorporate a recess in the area which will form or forms the reaction area. Regardless of configuration of the laminate member, means are further incorporated (on the laminate member or otherwise) that allow for the accurate and reliable positioning of the laminate member on the device, such as tape or adhesive.

FIG. 1 depicts an exploded view of a preferred embodiment of an example test strip. The base layer (1) is set out on the bottom. The dielectric coating (2) is depicted as positioned near one end of the exploded device, above the base layer. Together, elements 3–5(a & b) depict an exemplary electrode system. The first layer of the working carbon electrode (4a) is provided adjacent to the first layer of the counter electrode (4b). Two silver electrodes (3a & 3b) are depicted adjacent to one another, extending toward the first layer of the working and counter electrodes (4a & 4b). Above the silver electrodes (3a & 3b) the second layer of the working and counter electrodes (5a & 5b) are depicted. The insulating layer (6) is positioned over the electrode system. The test reagent (7) is depicted above the insulating layer. When positioned on the device in the reaction are, the test reagent (7) will be positioned on the dielectric coating. The laminate (9) incorporates an adhesive (8) for adherence to the assay device. An air aperture (11) and a sample supply aperture (10) are incorporated in/on the laminate (9) and adhesive (8).

Figure 2:
FIG. 2 depicts a fully assembled embodiment of an example test strip.

FIG. 2 depicts a fully assembled embodiment of an example test strip.

Although not required, the base member can be transparent. In such an embodiment, the liquid sample may be introduced on the opposite side of the transparent base member and the liquid sample movement can be monitored through the transparent base member.

The biosensor can further comprise an electron transfer mediator in the reaction area. Exemplary transfer mediators include ferrocene and its derivatives, osmium complex, tetrathiofulvalene, phenazine ethosulfate, benzoquinone or hexacyanoferrate.

In one embodiment, the biosensor can incorporate a "T-shaped" reaction area, wherein the non-reaction area at the distal end of the device is divided into two corner portions and one middle portion, and the middle portion is made part of the reaction area by an absence of dielectric material over and/or within the reaction area, whereby the reaction area occupies a T-shaped area comprising the complete cross-section of the base member in a direction perpendicular to said conductive leads and a strip area in a direction parallel to said conductive leading from the cross-section to the edge of the distal end.

The biosensor can have a "double slot" reaction area, wherein the non-reaction area at the distal end of the device is arranged into a single middle portion, this middle portion is made part of the reaction area by an absence of dielectric material over and/or within the reaction area, whereby the reaction area occupies a channel comprising the complete cross-section of the base member in a direction perpendicular to said conductive leads. Situated on each side of the middle portion are the sample application areas and venting means.

The biosensor can also have a "distal opening" reaction area, wherein the non-reaction area proximal to the second end is arranged into a single middle portion, this middle portion is made part of the reaction area by an absence of dielectric material over and/or within the reaction area, whereby the reaction area occupies a space comprising a portion of the base member encompassing a cross-section of the conductive leads. This area may extend in two directions, one extending to the distal end of the device, and the other extending in an opposite direction to an opening in the laminate member which is useful as a venting means.

The biosensor can optionally have a variety of reaction area configurations including the T-shape, in addition to double slot, distal opening, top, bottom and single slot configurations. Although a variety of configurations are contemplated, characteristics allowing for rapid sample introduction and temperature stability are frequently maintained.

In one embodiment, the present disclosure includes a biosensor for electrochemical analysis of a liquid sample wherein said electrode system comprises a working electrode, a counter electrode, and two reference electrodes, said working, counter and reference electrodes have conductive leads for connecting said electrodes to a readout device for electrochemical measurement on said first end of said base plate, each of said reference electrodes being diagonally positioned from said working or counter electrode and a gap space between said working/counter, working/reference and reference/reference electrodes, said working electrode and a first reference electrode diagonally positioned from said working electrode forms a first closed circuit and said counter electrode and a second reference electrode diagonally positioned from said counter electrode forms a second closed circuit, said first and second closed circuits are connected to form a third circuit, whereby said third circuit is closed only when both said first and second circuits are closed at the same time.

The working, counter and reference electrodes can be arranged in any suitable fashion. Preferably, the reference electrodes are engulfed by the working and counter electrodes on all sides except the side leading to said conductive leads. Also preferably, the reference electrodes are separated to the farthest distance without contacting either working or counter electrode. Alternatively, the reference electrodes can be on the outside and the working and counter electrodes can be on the inside.

The biosensor can further comprise a reaction area, wherein at least a portion of the working, counter and reference electrodes and the gap space among the electrodes comprise the reaction area, said reaction area comprises an enzyme that catalyzes a reaction involving an analyte to be analyzed or a substrate that is involved in a reaction catalyzed by an enzyme to be analyzed.

The present biosensors can prevent the incorrect result of analysis from insufficient volume or non-homogenous distribution of sample fluids. A fully established circuit generally requires that the sample fluid be well distributed to cover the working electrode and the counter electrode (and any reference electrodes located down stream of these electrodes). Furthermore, a non-homogenous distribution of sample fluid covering the reaction area partially is not able to establish the full circuit. The sample fluid from the counter electrode side has to cover the far end of the working electrode side to be able to establish the circuit and vise versa.

In one embodiment, the present invention provides a biosensor, which comprises an electrically insulating base member, two screen-printed electrodes consisting of a working one and counter one, and a reaction area including a test reagent having a hydrophilic component. The working electrode is formed in the reaction area and may be next to or surrounded by the counter electrode by a short, uniform distance. A pulse voltage applied to this working electrode activates the electrooxidation of sample and/or test reagent and the resulting electron flow is transduced as a measurable electric potential or electric signal.

Figure 7:
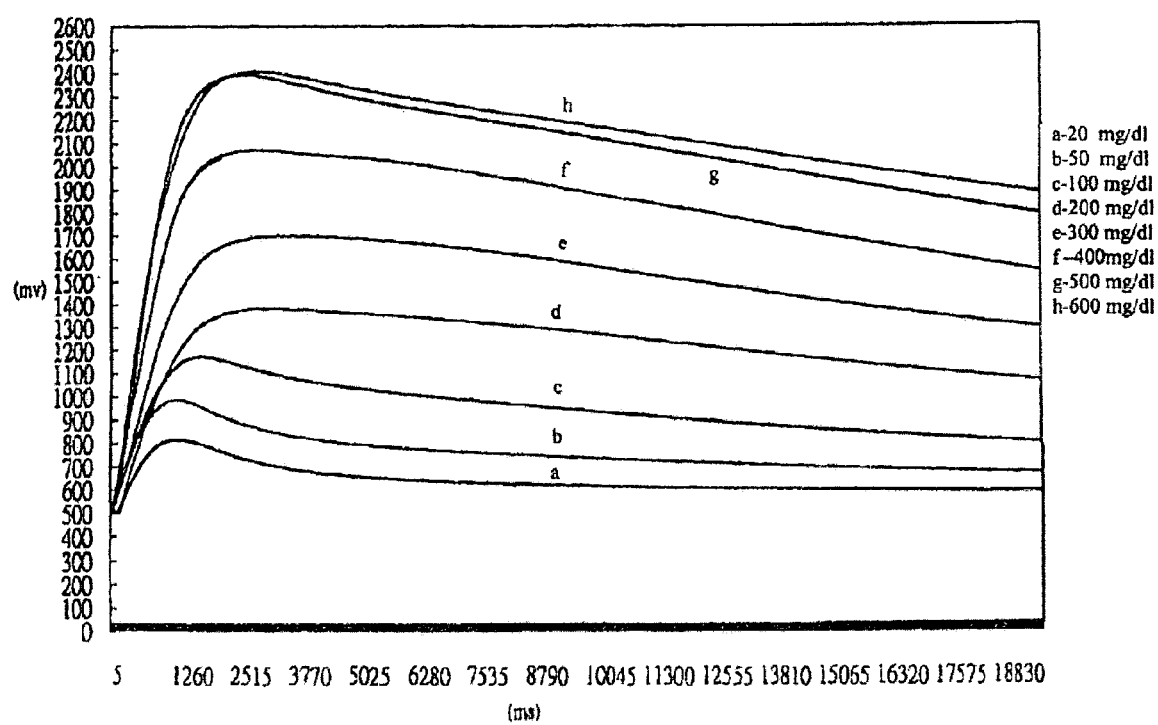
FIG. 7 provides a graph depiction of the voltage response over time (after contact of the sample with an exemplary test strip of the present description), for multiple samples, each having a different glucose concentration.

To achieve homogenous and quick reaction, sample loading is facilitated with the hydrophilic component of the test reagent. As indicated in FIG. 7, the loading time necessary to achieve a measurable and significant voltage is quite short, but the voltage is maintained over a period of time. FIG. 7 provides a graph depiction of the voltage response over time (after contact of the sample with an exemplary test strip of the present description), for multiple samples, each having a different glucose concentration. Independent samples containing glucose concentrations of 20 mg/dL, 50 mg/dL, 100 mg/dL, 200 mg/dL, 300 mg/dL, 400 mg/dL, 500 mg/dL and 600 mg/dL were evaluated.

Moreover, the sample application and venting means further facilitate sample loading into the reaction area. The loading of sample fluid is effected by contacting the sampling slot. On occasion, an arcuate portion of the slot protrudes into the reaction area to form a convex facing the reaction area. This is called a "loading convex" with the purpose to provide auxiliary propulsion by its outward surface tension. The lamina and the venting means provide a pull force for the sample fluids. With these features, only a minute amount of sample volume, e.g., 1.0 microliter, is required for a test. The quick draw of sample fluid, e.g., blood, to the reaction area ensures that a homogenous thin layer of sample fluid to be laid on top of the reaction layer, which ensures a rapid and uniform enzymatic reaction and a subsequent uniform generation of electronic flow.

Various other configurations are contemplated herein. In particular configurations the venting means may double as application means. Moreover, the vent may be located on the laminate member, formed by a punched hole through the laminate. In this configuration, adhesive is generally lacking below the punched hold to enable air flow. It is also another benefit of the present design to be able to pick up samples from alternative sites such as punctures at body parts other than fingersticks. Forearms, containing fewer nerves, can be an alternative sites for blood withdrawal, with less pain.

It is found that in the conventional method of introducing blood from fingersticks, the punctured fingerstick has to be located right on top of the sampling slot for the droplet of blood to be put into slot. This usually blocks the vision of the slot and thus frequently hinders a successful introduction of blood samples. It is even more handicapped for poor bleeders to be able to apply their scant blood by this method. In this invention, it is still another aspect that the sample fluid introduction can be done through the bottom side of the biosensor.

In the present biosensors, the reaction area contains a reagent mixture containing a hydrophilic component and an electrode system. Sample fluid is loaded into the sample application means and is immediately drawn to the reaction area. In a very short time, the test reagent dissolves and the enzymatic reaction proceeds. At the completion of, or concurrent with, the enzymatic reaction, a controlled-potential is applied between the electrodes to trigger another round of electrooxidation. After a short time delay, the electronic flow produced is measured and correlated to the presence or amount of the analyte in the sample fluid. Frequently, the time between sample contact with the sample application means and measurement of the electric potential generated comprises about 5 seconds. On occasion, the time between sample contact with the sample application means and measurement of the electric potential generated is less than 5 seconds. In utilizing the present devices, the time between sample application and measuring an electric potential is generally very short, for example, between about 1 second to about 10 seconds. See, e.g., FIG. 7. Although longer time lags can occur or be obtained, the present devices permit rapid and accurate measurement within a short period of time.

Two important features of the exemplary biosensors are the reaction area and sample application means. As the laminate member can have a thickness up to about 2 mm, the sampling slot is frequently fashioned as a depression in the laminate capable of serving as reservoir for sample fluids. An arcuate portion of this slot overlaps and protrudes into the reaction area to form a convex, often facing the test reagent. This loading convex provides auxiliary propulsion for the sample introduction with its outward surface tension. Since only this arcuate portion is left unsealed, it also serves as the only passage for the sample loading. The loaded sample fluid thus can only go unilaterally through the arcuate passage and no sample is wasted on non-reaction area. When the loaded sample fluids pass the loading convex, they are pulled upwardly and forwardly to fill the reaction layer with no hesitation. The pull-up forces are from the adhesion of the fluids, the test reagent, the boundaries of the reaction area, and/or the cohesion of the fluids themselves. The venting means provide air ventilation for this pull-up function.

Figure 5:
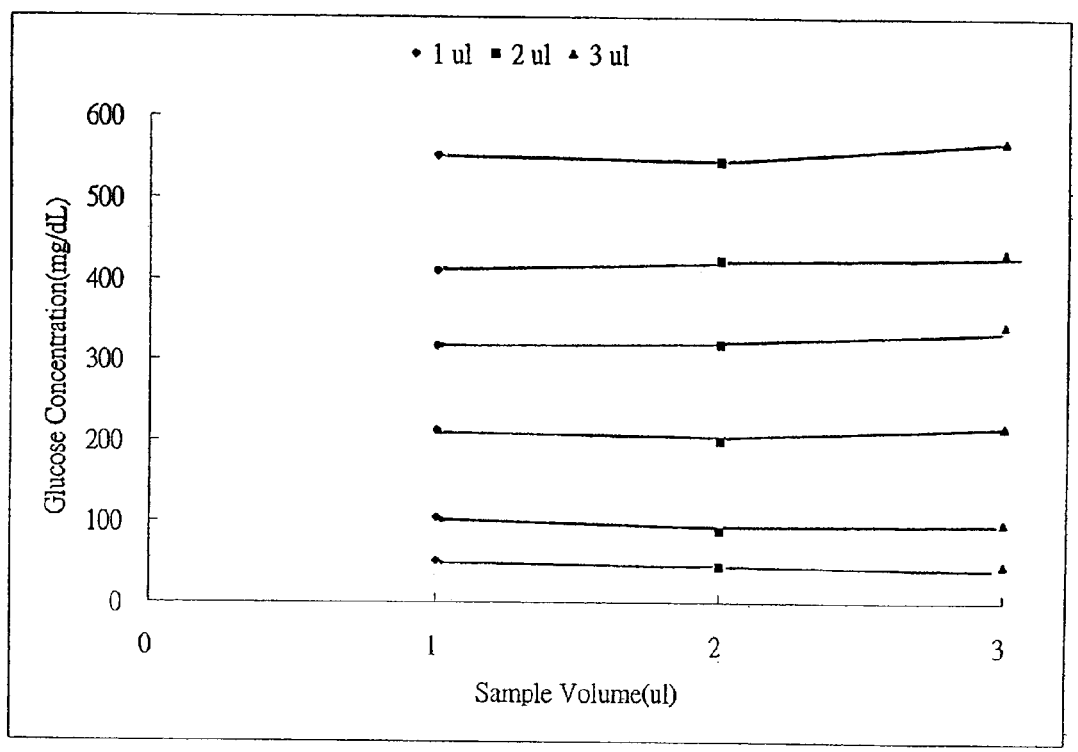
FIG. 5 provides a graph depiction of the average response given by a test strip in accordance with the present description across varying glucose concentrations while utilizing different sample volumes.
Figure 6:
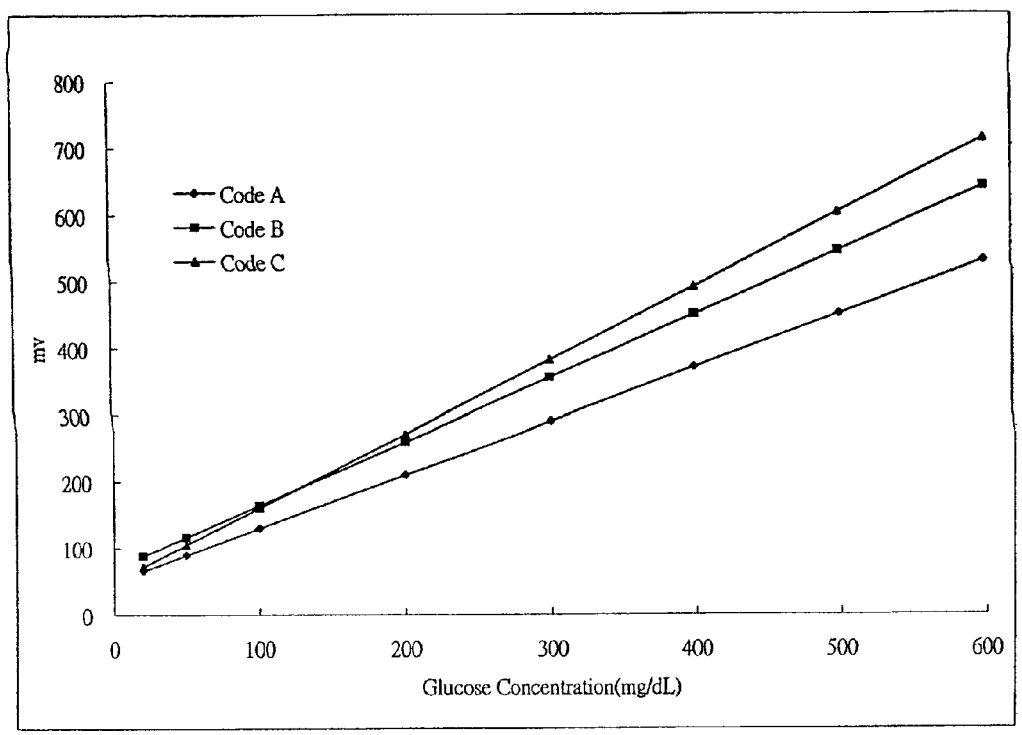
FIG. 6 illustrates hypothetical calibration curves for different lots of test strips.

The advantages of the present embodiments are numerous: For example, a minute amount of sample fluid, e.g., 1.0 microliter, is required for the test. As depicted in FIG. 5, sample volumes ranging from 1.0 to 3.0 microliters do not affect the consistency in glucose measurement in the present devices over a range of glucose concentrations. Further, the quick and effective drawing of blood over the reaction area generates a homogenous enzymatic reaction and a uniformly diffusion-dependent electrochemical reaction. Moreover, samples having a high concentration of analyte can be accurately analyzed. See, e.g., FIGS. 5–6.

An experiment may be therefore designed to test the efficiency of the sample application means and the reaction area together with the venting means to introduce sample into the reaction layer. When an aqueous sample is successfully introduced to the reaction area of a biosensor, a glucose meter is able to detect a change of current from the chemical reaction and proceeds the test. According to a glucose meter, e.g., GlucoSure, from Apex Biotechnology Co. (Taiwan), the successful sample introduction can be indicated by a beep sound to show a detection of the initial chemical reaction. A lag for the occurrence of the beep sound can thus be used to measure dose hesitation (i.e., a delay in sample introduction).

Before the laminate member is applied to the device, the test reagent including the hydrophilic component is prepared. A volume of 3 microliters of reagent is dispensed on the reaction layer, air-dried for 30 minutes with 45% humidity before being moved into a dry room for further drying. As a result, a uniform reaction layer is formed. The test starts with an introduction of sample fluid and the concentration of glucose is measured as the current generated through the electrooxidation.

Although the foregoing descriptions are all related to an amperometric glucose biosensor, this invention is widely applicable to an enzyme-related system such as cholesterol sensor, alcohol sensor, lactate sensor, etc. As mentioned above, the biosensor of the invention is capable of measuring a specific component in various kinds of samples rapidly. Moreover, the manufacturing process of present invention enables mass production of the biosensor strips with fairly simple procedures, low costs, and large volume of production.

Exemplary Uses of the Biosensors and the Assaying Methods

In one embodiment, a method is provided for assaying an analyte or an enzyme in a liquid sample, which method comprises: contacting a liquid sample containing or suspected of containing an analyte with the sample application means of a presently described biosensor under suitable conditions whereby an electric potential is generated; and detecting the generated electric potential, whereby the presence or amount of the analyte or enzyme in the sample liquid is assessed.

In a frequent embodiment, a method is provided for assaying an analyte or an enzyme in a liquid sample, which method comprises: a) contacting a liquid sample containing or suspected of containing an analyte or an enzyme with the above-described biosensor in the presence of a suitable test reagent under suitable conditions whereby the analyte in the sample liquid, if there is any, is involved in a reaction catalyzed by the enzyme comprised in the reaction area of the biosensor, or the enzyme in the sample liquid, if there is any, catalyzes a reaction involving the substrate comprised in the reaction area of the biosensor, said reaction involving the analyte or substrate, in conjunction with the electron transfer mediator, leads to the generation of a current that is capable of being detected by the biosensor; and b) detecting the current generated in step a), whereby the presence or amount of the analyte or enzyme in the sample liquid is assessed.

Any suitable volume of a liquid sample can be assayed by the present method. Preferably, the present method is used for assaying a small volume of a liquid sample. For example, the volume of the liquid sample to be assayed frequently is from about 1.0 microliter to about 10.0 microliters. Preferably, the volume of the liquid sample to be assayed is from about 1.0 microliter to about 3.0 microliters. Also frequently, the volume of the liquid sample contacted with the biosensor is more than about 1.0 microliter, but wherein the volume of sample the enters the reaction area is between about 1.0 microliter to about 3.0 microliters. Thus, a larger sample may be contacted with the device, but frequently only a portion of the larger sample enters the reaction area.

Any analyte that can be involved in an oxidizing or a reducing reaction or any enzyme that catalyzes an oxidizing or a reducing reaction can be assayed by the present method. For example, the analyte to be detected can be glucose. Frequently, the enzyme comprised in the reaction area of the biosensor is glucose oxidase and the electron transfer mediator used in the assay is potassium ferricyanide. When the analyte to be detected is glucose, frequently the glucose level in the sample is between about 20 mg/dL to about 600 mg/dL. On occasion, the glucose level in the sample is between about 300 mg/dL to about 600 mg/dL. Also on occasion, the glucose level in the sample is above 600 mg/dL, up to about 700 mg/dL, or more. Devices and methods of the present disclosure enable the accurate reading of samples having high analyte (e.g., glucose) concentrations, frequently ranging above 300 mg/dL.

In a specific embodiment, the present invention is directed to a method for assaying an analyte or an enzyme in a liquid sample, which method comprises: a) contacting a liquid sample containing or suspected of containing an analyte or an enzyme with the presently described biosensor which contains a suitable test reagent in the reaction area under suitable conditions whereby the analyte in the sample liquid, if there is any, is involved in a reaction catalyzed by an enzyme comprised in the reaction area of the biosensor, or the enzyme in the sample liquid, if there is any, catalyzes a reaction involving the substrate comprised in the reaction area of the biosensor, said reaction involving the analyte or substrate leads to the generation of a current that is capable of being detected by the biosensor; and b) detecting the current generated in step a), whereby the presence or amount of the analyte or enzyme in the sample liquid is assessed.

In another specific embodiment, the present invention is directed to a method for assaying an analyte or an enzyme in a liquid sample, which method comprises: a) contacting a liquid sample containing or suspected of containing an analyte or an enzyme with the above-described biosensor which contains a "T-shaped," "double slot," "distal opening," "top," "bottom" or "single slot" reaction area in the presence of a suitable test reagent under suitable conditions whereby the analyte in the sample liquid, if there is any, is involved in a reaction catalyzed by the enzyme comprised in the reaction area of the biosensor, or the enzyme in the sample liquid, if there is any, catalyzes a reaction involving the substrate comprised in the reaction area of the biosensor, said reaction involving the analyte or substrate leads to the generation of a current that is capable of being detected by the biosensor; and b) detecting the current generated in step a), whereby the presence or amount of the analyte or enzyme in the sample liquid is assessed.

The present biosensors and methods can be used to qualitatively or quantitatively detect any analyte or enzyme. For example, the analyte to be assayed can be macromolecules such as peptides, proteins, e.g., antibodies or receptors, oligonucleotides, nucleic acids, vitamins, oligosaccharides, carbohydrates, lipids, or small molecules, or a complex thereof. Exemplary proteins or peptides include enzymes, transport proteins such as ion channels and pumps, nutrient or storage proteins, contractile or motile proteins such as actins and myosins, structural proteins, defense proteins or regulatory proteins such as antibodies, hormones and growth factors. Exemplary nucleic acids include DNA, such as A-, B- or Z-form DNA, and RNA such as mRNA, tRNA and rRNA. The nucleic acids can be single-, double- and triple-stranded nucleic acids. Exemplary vitamins include water-soluble vitamins such as thiamine, riboflavin, nicotinic acid, pantothenic acid, pyridoxine, biotin, folate, vitamin $B_{12}$ and ascorbic acid, and fat-soluble vitamins such as vitamin A, vitamin D, vitamin E, and vitamin K. Exemplary lipids include triacylglycerols such as tristearin, tripalmitin and triolein, waxes, phosphoglycerides such as phosphatidylethanolamine, phosphatidylcholine, phosphatidylserine, phosphatidylinositol and cardiolipin, sphingolipids such as sphingomyelin, cerebrosides and gangliosides, sterols such as cholesterol and stigmasterol and sterol fatty acid esters. The fatty acids can be saturated fatty acids such as lauric acid, myristic acid, palmitic acid, stearic acid, arachidic acid and lignoceric acid, or can be unsaturated fatty acids such as palmitoleic acid, oleic acid, linoleic acid, linolenic acid and arachidonic acid.

Preferably, the analyte or enzyme to be detected is a marker for a biological pathway, a stage of cell cycle, a cell type, a tissue type, an organ type, a developmental stage, a disease, disorder or infection type or stage, or drug or other treatments. Exemplary tissues include connective, epithelium, muscle or nerve tissues. Exemplary organs include an accessory organ of the eye, annulospiral organ, auditory organ, Chievitz organ, circumventricular organ, Corti organ, critical organ, enamel organ, end organ, external female gential organ, external male genital organ, floating organ, flower-spray organ of Ruffini, genital organ, Golgi tendon organ, gustatory organ, organ of hearing, internal female genital organ, internal male genital organ, intromittent organ, Jacobson organ, neurohemal organ, neurotendinous organ, olfactory organ, otolithic organ, ptotic organ, organ of Rosenmuller, sense organ, organ of smell, spiral organ, subcommissural organ, subfornical organ, supernumerary organ, tactile organ, target organ, organ of taste, organ of touch, urinary organ, vascular organ of lamina terminalis, vestibular organ, vestibulocochlear organ, vestigial organ, organ of vision, visual organ, vomeronasal organ, wandering organ, Weber organ and organ of Zuckerkandl can be manipulated. Exemplary internal animal organs include brain, lung, liver, spleen, bone marrow, thymus, heart, lymph, blood, bone, cartilage, pancreas, kidney, gall bladder, stomach, intestine, testis, ovary, uterus, rectum, nervous system, gland, internal blood vessels. Exemplary diseases or disorders include neoplasm (neoplasia), cancers, immune system diseases or disorders, metabolism diseases or disorders, muscle and bone diseases or disorders, nervous system diseases or disorders, signal diseases or disorders, transporter diseases or disorders.

Analyte from any fluid sample can be detected by the present method. Exemplary liquid sample include buffer, blood, serum, plasma, or urine, or a solution or suspension containing solid or gaseous biological material.

Manufacturing Methods

In one embodiment, a method of manufacturing the presently described devices is provided. Such a method frequently comprises: applying the dielectric coating to the base member; applying the electrode system to the base member and over a portion of the dielectric coating; applying the dielectric layer to the base member and over at least a portion of the electrode system but not within the reaction area; applying the test reagent to at least a portion of the dielectric coating within the reaction area; and adhering the laminate member to the dielectric layer. Frequently, the dielectric coating, the electrode system and/or the dielectric layer are applied via a screen-printing method.

Other methods of manufacturing are contemplated and are dependant on the desired device configurations.

The above embodiments are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

What is claimed is:

1. A biosensor for electrochemical analysis of a liquid sample, which biosensor comprises:
    a) a base member having a proximal and a distal end;
    b) a laminate member having a proximal and a distal end positioned in vertical, parallel alignment with said base member, wherein the laminate member defines a venting means and a sample application means positioned over said distal end of said laminate, and wherein said distal end of said laminate member is aligned with said distal end of said base member;
    c) an electrode system positioned between said base member and said laminate member, wherein said electrode system comprises a working electrode and a counter electrode, said working and counter electrodes having conductive leads at said proximal end of said base member for connecting said electrodes to a readout device for electrochemical measurement, wherein said working electrode is positioned adjacent to said counter electrode, and there is a gap space between said working and counter electrodes;
    d) an insulating layer positioned between said base member and said laminate member;
    e) a reaction area positioned between said base member and said laminate member, which reaction area encompasses at least a portion of said working electrode, said counter electrode and the gap space between said working electrode and said counter electrode, wherein the reaction area is defined by an opening between said base member and said laminate member, and which reaction area has a test reagent positioned therein; and
    f) a dielectric coating positioned between said electrode system and said base member and within at least a portion of the reaction area,
    wherein the test reagent comprises a liquid soluble hydrophilic component.

2. The biosensor of claim 1, wherein the test reagent is positioned to overlap at least a portion of the working electrode and the counter electrode, and wherein, when the test reagent is positioned, any portion of the test reagent not overlapping the working and counter electrodes is positioned on the dielectric coating.

3. The biosensor of claim 1, wherein the reaction area is further defined by a recess positioned in the laminate member between the sample application means and the venting means.

4. The biosensor of claim 3, wherein the reaction area comprises an opening in the biosensor having internal boundaries comprising the laminate member and the dielectric coating as opposing boundaries and a lateral boundary between the laminate member and the dielectric coating comprising the insulating layer together with a portion of the recess in the laminate member.

5. The biosensor of claim 3, wherein the working and counter electrodes are carbon coated.

6. The biosensor of claim 5, wherein the working and counter electrodes have two or more coatings of carbon at the portion encompassed by the reaction area.

7. The biosensor of claim 3, wherein the sample application means comprises one or more openings that allow fluid communication with the reaction area for sample application.

8. The biosensor of claim 1, wherein said insulating layer and said dielectric coating are comprised of the same materials.

9. The biosensor of claim 1, wherein said reaction area comprises a complete cross-section of a portion of the electrode system.

10. The biosensor of claim 1, wherein the laminate member is comprised of polyurethane or polyethylene.

11. The biosensor of claim 1, wherein the test reagent fiiLrther comprises a surfactant and citric acid.

12. The biosensor of claim 1, wherein the liquid soluble hydrophilic component comprises polyvinylpyridine (PVP).

13. The biosensor of claim 1, wherein the liquid soluble hydrophilic component comprises PVP.

14. The biosensor of claim 1, wherein the base member comprises vinyl polymer(s), polymide(s), polyester(s), nylon, nitrocellulose or a combination thereof.

15. The biosensor of claim 1, further comprising an electron transfer mediator disposed in the reaction area.

16. The biosensor of claim 15, wherein the electron transfer mediator is selected from the group consisting of ferrocene and its derivatives, osmium complex, tetrathiofulvalene, phenazine ethosulfate, benzoquinone and hexacyanoferrate.

17. The biosensor of claim 1, wherein the working and counter electrodes are comprised of substantially identical material(s) within the reaction area.

18. The biosensor of claim 1, wherein the gap space between the working electrode and the counter electrode is substantially constant within the reaction area.

19. The biosensor of claim 1, wherein the electrode system is screen-printed onto the base member.

20. The biosensor of claim 19, wherein the working and counter electrodes comprise carbon paste and the conductive leads comprise conductive silver paste.

21. The biosensor of claim 1, wherein the base member and/or the laminate member is/are transparent.

22. The biosensor of claim 1, wherein the reagent further comprises an enzyme that catalyzes a reaction involving an analyte of interest or a substrate that is involved in a reaction catalyzed by an enzyme of interest.

23. The biosensor of claim 1, wherein the dielectric coating comprises 10–30% talc, 15–40% dicyclopentenyloxyethyl acrylate and 1–5% polydimethylsiloxane/silica adduct.

24. A method for assaying an analyte or an enzyme in a liquid sample, which method comprises:
   a) contacting a liquid sample containing or suspected of containing an analyte with the sample application means of the biosensor of claim 1 under suitable conditions whereby an electric potential is generated; and
   b) detecting the electric potential generated in step a), whereby the presence or amount of the analyte or enzyme in the sample liquid is assessed.

25. The method of claim 24, wherein the volume of the liquid sample contacted with the biosensor is between about 1.0 microliter and about 3.0 microliters.

26. The method of claim 24, wherein the volume of the liquid sample contacted with the biosensor is more than about 1.0 microliter, but wherein the volume of sample the enters the reaction area is between about 1.0 microliter to about 3.0 microliters.

27. The method of claim 24, wherein the analyte to be detected is glucose.

28. The method of claim 27, wherein the glucose level in the sample is between about 20 mg/dL to about 600 mg/dL.

29. The method of claim 24, wherein the liquid soluble hydrophilic component comprises PVP.

30. A method for manufacturing the bioassay device of claim 1, which method comprises:
   applying the dielectric coating to the base member;
   applying the electrode system to the base member and over a portion of the dielectric coating;
   applying the insulating layer to the base member and over at least a portion of the electrode system but not within the reaction area;
   applying the test reagent to at least a portion of the dielectric coating within the reaction area; and
   adhering the laminate member to the insulating layer.

31. The method of claim 30, wherein the dielectric coating, the electrode system and the insulating layer are applied via screen-printing.

32. The method of claim 30, wherein the liquid soluble hydrophilic component comprises polyvinylpyridine.

33. The biosensor of claim 1, wherein said insulating layer and said dielectric coating are comprised of different materials.

* * * * *